(12) United States Patent
Stewart et al.

(10) Patent No.: US 7,388,200 B2
(45) Date of Patent: Jun. 17, 2008

(54) SENSING METHOD AND NANOSENSING DEVICE FOR PERFORMING THE SAME

(75) Inventors: Duncan R. Stewart, Palo Alto, CA (US); William M. Tong, Palo Alto, CA (US); R. Stanley Williams, Palo Alto, CA (US); Philip J. Kuekes, Palo Alto, CA (US); Sean Xiao-an Zhang, Palo Alto, CA (US); Kevin F. Peters, Corvallis, OR (US); Kenneth J. Ward, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/583,262

(22) Filed: Oct. 19, 2006

(65) Prior Publication Data
US 2008/0116490 A1     May 22, 2008

(51) Int. Cl.
*G01N 27/26* (2006.01)
*G01N 33/00* (2006.01)

(52) U.S. Cl. ............... 250/306; 250/307; 204/400; 977/762; 977/957

(58) Field of Classification Search ............. 977/762, 977/904, 953–960; 204/400; 250/306, 307
See application file for complete search history.

(56) References Cited

U.S. PATENT DOCUMENTS

| | | | | |
|---|---|---|---|---|
| 6,325,904 B1* | 12/2001 | Peeters | ................. | 257/414 |
| 6,673,533 B1* | 1/2004 | Wohlstadter et al. | ........... | 435/6 |
| 7,129,554 B2* | 10/2006 | Lieber et al. | ................. | 257/414 |
| 7,186,381 B2* | 3/2007 | Penner et al. | ................. | 422/98 |
| 7,211,464 B2* | 5/2007 | Lieber et al. | ................. | 438/99 |
| 7,256,466 B2* | 8/2007 | Lieber et al. | ................. | 257/414 |
| 2005/0070802 A1* | 3/2005 | Peters et al. | ................. | 600/459 |
| 2005/0241959 A1* | 11/2005 | Ward et al. | ................. | 205/792 |
| 2006/0024814 A1* | 2/2006 | Peters et al. | ............. | 435/287.2 |
| 2006/0054936 A1* | 3/2006 | Lieber et al. | ................. | 257/210 |
| 2006/0175601 A1* | 8/2006 | Lieber et al. | ................. | 257/19 |
| 2006/0269927 A1* | 11/2006 | Lieber et al. | ................. | 435/6 |
| 2007/0015151 A1* | 1/2007 | Schrenzel et al. | ............. | 435/6 |
| 2007/0045667 A1* | 3/2007 | Lieber et al. | ................. | 257/211 |
| 2007/0089516 A1* | 4/2007 | Khuri-Yakub et al. | ........ | 73/579 |

OTHER PUBLICATIONS

Hahm, J. et al., "Direct Ultrasensitive Electrical Detection of DNA and DNA Sequence Variations Using Nanowire Nanosensors," Nano Lett., vol. 4, No. 1, 2004, pp. 51-54.
Sheehan, P. E. et al., "Detection Limits of Nanoscale Biosensors," Nano Lett., vol. 5, No. 4, 2005, pp. 803-807.
Li, Z. et al., "Silicon Nanowires for Sequence-Specific DNA Sensing: Device Fabrication and Simulation," Appl. Phys. A 80, 2005, pp. 1257-1263.

* cited by examiner

*Primary Examiner*—John R Lee (57) ABSTRACT

A sensing method includes exposing a nano-transducer having a controlled surface to a sample including at least one species. Adsorption of the species on the nano-transducer is transduced to a measurable signal as a function of time. Desorption of the species from the nano-transducer is also transduced to a measurable signal as a function of time. A residence time of the at least one species adsorbed on the nano-transducer is extracted from the measurable signals. The adsorption and desorption each define an individual measurable event.

27 Claims, 6 Drawing Sheets

NANO-TRANSDUCER
DISCLOSED HEREIN

OTHER
TRANSDUCERS

SENSING METHOD AND NANOSENSING DEVICE FOR PERFORMING THE SAME

BACKGROUND

The present disclosure relates generally to sensing methods and a nanosensing system for performing the same.

Since the inception of semiconductor technology, a consistent trend has been toward the development of smaller device dimensions and higher device densities. As a result, nanotechnology has seen explosive growth and generated considerable interest. Nanotechnology is centered on the fabrication and application of nano-scale structures, or structures having dimensions that are often 50 to 100 times smaller than conventional semiconductor structures. Generally, nano-scale structures have at least one linear dimension ranging from about 1 nm to about 100 nm.

Nano-scale structures have been employed as chemical and/or biological sensors in a wide variety of implementations, often operating by transducing adsorption of a species onto a target surface into an electrical, optical or mechanical signal. Nanowires are wire-like structures that are included in the category of nano-scale structures. Nanowires are suitable for use in a variety of nano-scale devices, such as nano-scale field effect transistors (FETs), p-n diodes, light emitting diodes (LEDs) and nanowire-based sensors, to name a few. Generally, nano-scale sensors are optimized for detecting specific species by specific preparation of the adsorption surface, for example, by coating the surface with specific receptors. However, the use of nanosensors as commercial devices remains limited, in many cases, by the differential specificity that individual sensors exhibit toward different chemical species.

BRIEF DESCRIPTION OF THE DRAWINGS

Features and advantages of the present disclosure will become apparent by reference to the following detailed description and drawings, in which like reference numerals correspond to similar, though not necessarily identical components. For the sake of brevity, reference numerals or features having a previously described function may not necessarily be described in connection with other drawings in which they appear.

DETAILED DESCRIPTION

Differential specificity may be desirable for nanosensing systems. A system with differential specificity has individual sensors within an ensemble that are advantageously able to detect different chemical species. Embodiment(s) of the sensing system and method disclosed herein incorporate such sensors, and thus are useful for obtaining significantly enhanced differential specificity to various species for the purposes of their identification and quantification.

Embodiments of the sensing system and method disclosed herein advantageously combine nano-scale sensors, kinetic adsorption and desorption rate characterization, and temperature control. The nano-scale sensors have the capability of transducing the adsorption and desorption of a variety of different species to measurable signals as a function of time. Well-known statistical methods (e.g., principle components regression, partial least squares, nonlinear regression, etc.) may be applied to the measurable signals. The statistical data, in conjunction with reference libraries of nanosensor responses to known species, may be used to quantify and/or identify the species.

Figure 1:
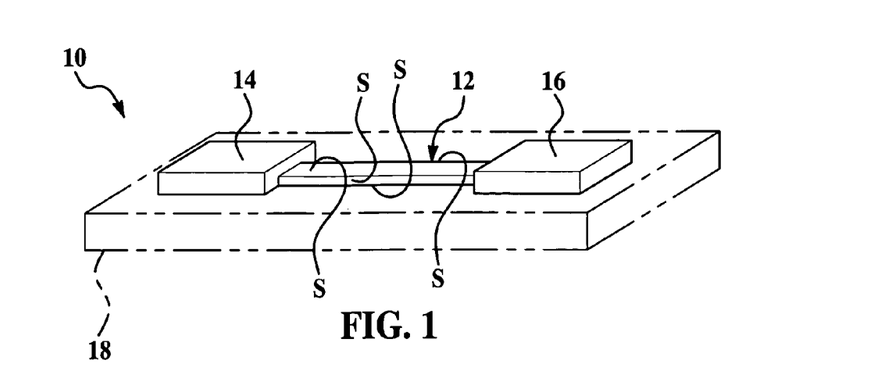
FIG. 1 is semi-schematic perspective view of an embodiment of the sensing system.
Figure 2:
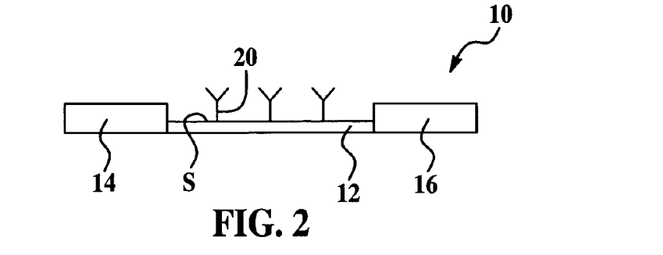
FIG. 2 is a schematic side view of an embodiment of the sensing system including receptors.

Referring now to FIG. 1, an embodiment of the sensing system 10 is depicted. Generally, an embodiment of the sensing system 10 includes a nano-transducer 12 having a controlled surface S. In an embodiment, the surface S is dynamically controlled, for example, by modification of thermal, optical, or electrical conditions. As depicted in FIG. 1, any exposed surface of the nano-transducer 12 may be a controlled surface S. As used herein, the term "controlled surface" refers to a surface that is prepared or modified for adsorption and desorption of numerous species (i.e., atoms, ions, molecules, chemical complexes, biological complexes, etc.) of interest. The controlled surface S may have receptors established thereon (described further in reference to FIG.

2), a predetermined atomic composition (e.g., oxides, nitrides, hydrogen terminated coatings, inorganic or organic monolayer coatings, or combinations thereof), a predetermined nanostructure (e.g., porous silicon shell, packed monolayer, dense thermal oxide, or the like), or combinations thereof.

The nano-transducer 12 has at least two linear dimensions (e.g., length, width, height, etc.) that are nanometer scale dimensions. The nanometer scale generally ranges from about 1 nm to about 100 nm. A non-limiting example of a nano-transducer 12 is a nanowire. The nanowire may be formed of one or more metals, one or more semi-conductor materials, one or more insulating materials, or combinations thereof. Other examples of suitable nano-transducers 12 include carbon nanotubes, nanoparticles, quantum dots, and/or the like, and/or combinations thereof.

The sensing system 10 shown in FIG. 1 is an embodiment of an electrical sensing system in which the nano-transducer 12 is operatively connected to electrodes 14, 16. An electrical sensing system may be configured to transduce adsorption and desorption of a species on, and from the nano-transducer 12 to measurable electrical signals, so as to determine resistance, inductance, and/or capacitance. As a non-limiting example, if the nano-transducer 12 is configured to determine resistance, when nothing is adsorbed on the nano-transducer surface S, the nano-transducer 12 is in an initial state, and a corresponding signal is exhibited. When a species adsorbs on the nano-transducer 12, it modifies the nano-transducer 12, thereby causing the signal to exhibit more or less electrical current (depending on the species adsorbed) than when the species is not adsorbed thereon. Upon desorption of the species, the nano-transducer 12 is unmodified (i.e., returns to its initial state), and the signal changes to reflect the same.

It is to be understood that the electrodes 14, 16 shown in FIG. 1 may not be included in other embodiments of the sensing system 10, for example, in optical sensing systems and mechanical sensing systems.

Embodiment(s) of the optical sensing system disclosed herein may include nano-transducers 12 that reflect, absorb, and/or emit light. The optical sensing systems may be configured to transduce adsorption and desorption of a species to optical signals, so as to determine one or more of absorption, reflectance, emission (e.g., fluorescence or phosphorescence), Raman scattering, other signals via spectroscopic methods, or combinations thereof. As a non-limiting example of a nano-transducer 12 that is configured to determine reflectance, when nothing is adsorbed on the nano-transducer surface S, the nano-transducer 12 is in an initial state, and a corresponding signal (indicative of reflectance at the initial state) is exhibited. When a species adsorbs on the nano-transducer 12, it causes a decrease in the reflectance from that exhibited when the species is not adsorbed thereon. Desorption of the species causes the nano-transducer 12 to revert back to its initial state, and the signal reflects this reversion.

Embodiments of the mechanical sensing system disclosed herein may include nano-transducers 12 that are operatively connected to a mechanical support, such as a cantilever or bridging unit. The mechanical sensing systems may be configured to transduce adsorption and desorption of a species as a function of stress or frequency. As a non-limiting example, if the nano-transducer 12 is designed to determine frequency, when nothing is adsorbed on the nano-transducer surface S, the nano-transducer 12 is in an initial state, and a corresponding signal (indicative of the frequency at the initial state) is exhibited. When a species adsorbs on the nano-transducer 12, it causes a decrease in the frequency as compared to when the species is not adsorbed thereon. Upon desorption of the species, the nano-transducer 12 is returned to its initial state, and the signal reverts back to its initial value.

The sensing system 10 shown in FIG. 1 is also established on a substrate 18. In another embodiment, the nano-transducer 12 is a freely suspended structure that is not supported by a substrate 18. The freely suspended structure may be particularly suitable for an embodiment of the mechanical sensing system that senses stress applied to the nano-transducer 12.

Referring now to FIG. 2, an embodiment of the sensing system 10 includes one or more receptors 20 established thereon. In an embodiment, the receptors 20 are established as a coating on the nano-transducer 12, thereby providing the nano-transducer 12 with a controlled surface S. The receptors 20 are incorporated into the sensing system 10 to functionalize the nano-transducer 12 for preferential and/or differential adsorption and desorption of the one or more species. As such, the receptor(s) 20 selected may be dependent upon, at least in part, the target species. Non-limiting examples of suitable receptors 20 include electron acceptors, electron donors, aromatic materials, polar groups, bioreceptors, bioactive receptors, charged species, or combinations thereof.

As previously described, the receptors 20 (as shown in FIG. 2), the atomic composition, the nanostructure (e.g., nano-scale texture), or combinations thereof may be selected to obtain a desirable controlled surface S. It is to be understood that the atomic composition and/or the nanostructure of the receptors 20 may also be controlled so that one or more target species will adsorb on, and desorb from the receptors 20. Further, it is to be understood that in addition to, or as an alternative to including receptors 20, the atomic composition and/or nanostructure of the nano-transducer 12 may be controlled so that one or more target species will adsorb on, and desorb from the controlled surface S.

The receptors 20 or the other controlled surfaces S are selected to produce a relatively large dynamic range of signal. The capture rate of the species (shown as 22 in FIGS. 3A-3C) influences the dynamic range.

Figure 3A:
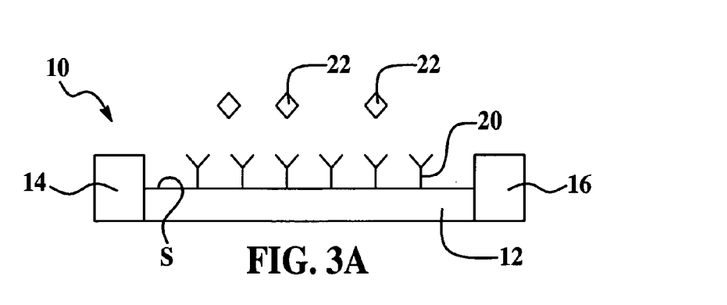
FIGS. 3A through 3C depict schematic diagrams of a species respectively adsorbing on, residing on, and desorbing from a receptor of an embodiment of the sensing system.
Figure 3B:
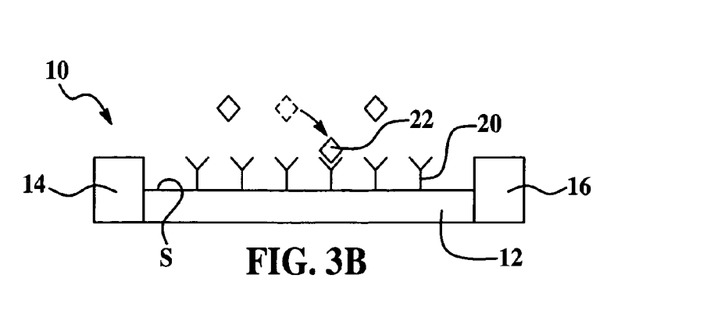
Figure 3C:
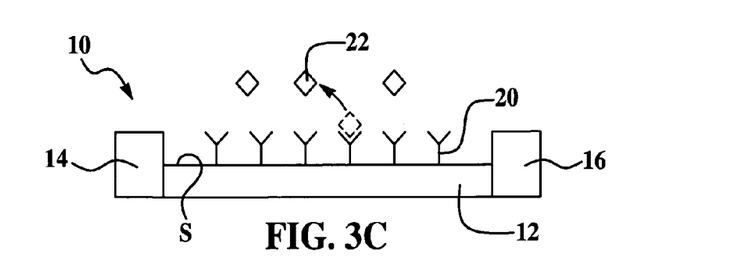

Referring now to FIGS. 3A through 3C together, an embodiment of the method illustrating adsorption and desorption of a species 22 on and from the nano-transducer 12 is depicted. In this embodiment, the nano-transducer 12 includes receptors 20 which provide the controlled surface S. The receptors 20 are selected for preferential and/or differential adsorption and desorption of one or more species 22.

Generally, the sample (including the species 22) is diluted so that the nano-transducer 12 does not become saturated, and so that integral adsorption and desorption events are observable.

Upon introduction of the sample to the controlled surface S of the nano-transducer 12, the species 22 adsorbs on a receptor 20 (as shown in FIG. 3B) that is capable of adsorbing a species 22 of interest. As a non-limiting example, if the species is an electron donating group (e.g., —OH), the receptor 20 may be an electron accepting group (e.g., $BCl_2$). The species 22 will desorb, as shown in FIG. 3C, from the receptor 20 at a rate characteristic of the attachment between the species 22 and the receptor 20 (or other controlled surface S).

Adsorption of the species 22 on the receptor 20 (or the controlled surface S) is recognizable by the nano-transducer 12. As previously described, the adsorption causes some electrical, optical or mechanical change that is detected by the nano-transducer 12. The nano-transducer 12 is capable of transducing the adsorption to a measurable signal as a function of time. Desorption of the species 22 from the receptor 20 (or other controlled surfaces S) is also recognizable by the nano-transducer. The desorption also causes a detectable electrical, optical or mechanical change in the nano-transducer 12. The nano-transducer 12 is capable of transducing the desorption to a measurable signal as a function of time.

Figure 3D:
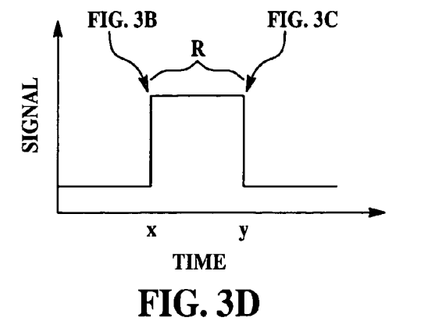
FIG. 3D depicts an example of a graph showing the signals resulting from adsorption and desorption.

It is to be understood that adsorption and desorption each define an individual measurable event. It is to be further understood that an individual measurable event includes a small integer number (e.g., 1, 2, 3, 4 or 5) of adsorptions, desorptions, or combinations thereof. These individual events may be plotted as a function of time, similar to a telegraph signal. FIG. 3D depicts the plotted "events" of FIGS. 3B and 3C. As a non-limiting example, the adsorption of species 22, as shown in FIG. 3B, causes the signal to rise at time "X". The desorption of species 22, as shown in FIG. 3C, causes the signal to fall at time "Y". From these signals, a residence time R of adsorption of the species 22 may be determined. The residence time R is time that elapsed between "X" and "Y", which is indicative of the time that the species 22 remains adsorbed on the nano-transducer 12.

Figure 3E:
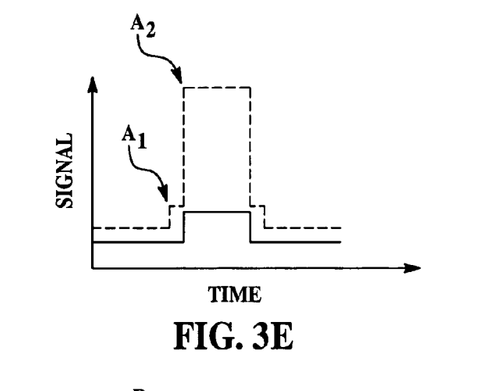
FIG. 3E depicts an example of a graph showing two substantially simultaneous adsorption events, and the corresponding detectable signal.

The nano-transducer 12 is capable of transducing numerous events. The response of the nano-transducer 12 may be non-linear in the number of simultaneous adsorptions detected. In FIG. 3E, an example of two substantially simultaneous adsorption and desorption events is shown as a dotted line, and an example of the transduced signal is shown as a solid line. In this non-limiting example, the first adsorption $A_1$ may be a small, undetectable signal, while the second substantially simultaneous adsorption $A_2$ may be transduced into a larger, detectable signal. The system 10 transduces the second event, which (as shown by the solid line) resembles a single individual event in the output signal. It is to be understood however, that without the first adsorption $A_1$, the second adsorption $A_2$ would likely not have been visible. Without being bound to any theory, it is believed that individual events that include a small integer number of adsorptions and/or desorptions are also useful for species 22 identification and/or quantification.

Figures 3F, 3G:
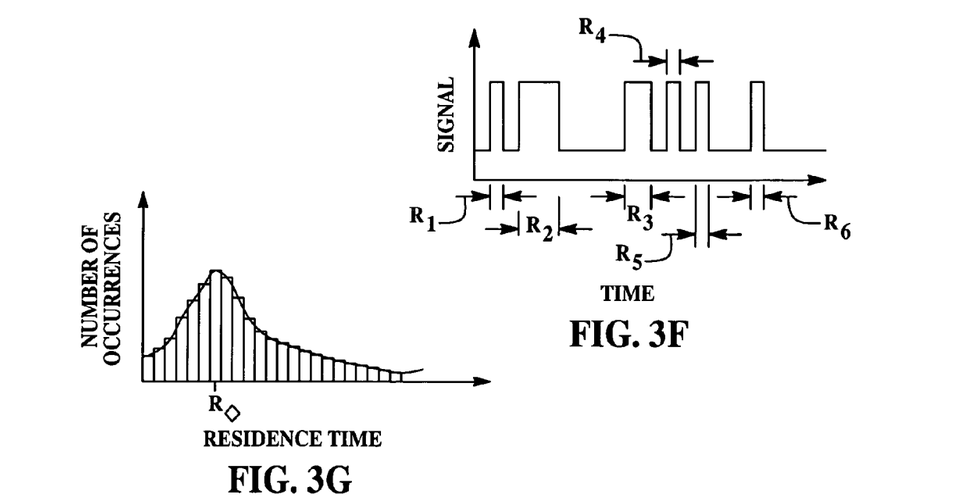
FIG. 3F depicts an example of a telegraph signal of multiple sequential adsorbing and desorbing events and residence times.
FIG. 3G depicts an example of a histogram showing a distribution of residence times.
Figure 4A:
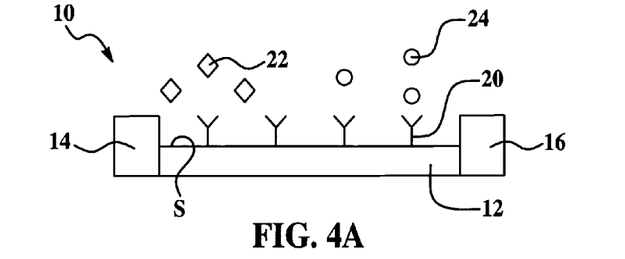
FIG. 4A is a schematic side view of an embodiment of the sensing system including receptors being exposed to two different species.

FIG. 3F depicts an example of a signal versus time graph for a series of sequential events that are detected by the nano-transducer 12. In this embodiment, each rise in the signal is indicative of an adsorption event, and each fall in the signal is indicative of a desorption event. In an alternate embodiment, each fall in the signal is indicative of an adsorption event, and each rise in the signal is indicative of a desorption event. It is to be understood that the events may be indicative of a single species 22 or of a variety of species 22, 24 (species 24 is shown in FIG. 4A). As previously described, the residence times R for each pair of events (labeled $R_x$, where x=1, 2, 3, 4, 5 or 6) may be extracted from these measurable signals.

Statistical distributions may be extracted from two or more pairs of individual adsorption and desorption events and the corresponding residence times R. The histogram depicted in FIG. 3G represents the distribution of the residence times R for a series of multiple sequential events (similar to those shown in FIG. 3F). The statistical distributions of residence times are likely to be Poisson or Poisson-like distributions. The number of occurrences is plotted against the residence time. Analysis of the distribution of residence times assists in substantially identifying the target species 22, as the kinetic capture (adsorption) and release (desorption) rates are characteristic of each species 22 and each surface S.

As depicted in FIG. 3G, the target species 22 (represented by the diamond shape) has numerous instances of residence times corresponding to the time at the peak of the distribution curve. Those portions of the curve furthest away from the peak (in either direction) indicate that for these times, there were relatively few instances of residence times corresponding thereto.

Referring now to FIG. 4A, the embodiment of the sensing system shown in FIG. 3A is exposed to a sample containing two different species 22, 24. It is to be understood that the controlled surface S of the nano-transducer may be selected to preferentially and/or differentially adsorb and desorb one or both of the species 22, 24. As previously described in reference to FIGS. 3D through 3F, the adsorption and desorption events of the species 22, 24 are transduced by the nano-transducer 12 to measurable electrical, optical or mechanical signals. These signals may be plotted as a function of time to determine the residence times R of each of the species 22, 24.

Figures 4B, 5A, 5B, 5C:
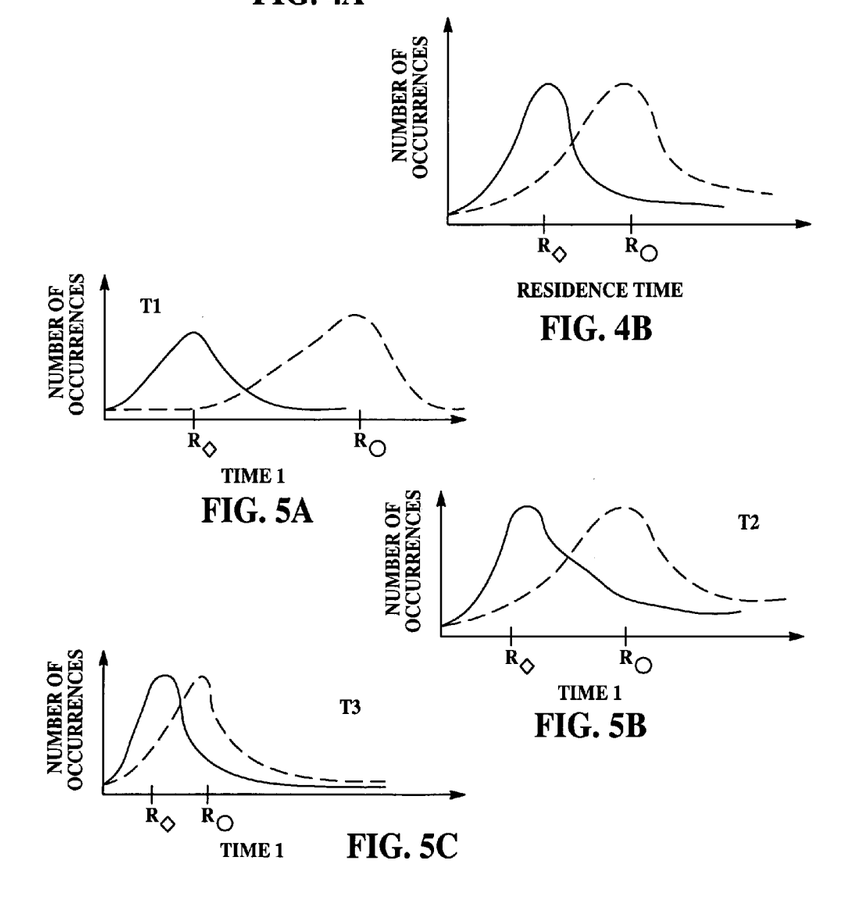
FIG. 4B depicts an example of a distribution of residence times for two different species.
FIGS. 5A, 5B and 5C depict graphs illustrating how a change in temperature is capable of altering a distribution of residence times of two different species.

FIG. 4B depicts an example embodiment of residence time distribution graphs extracted from the pairs of individual events and the determined residence times $R(R_\diamond, R_\circ)$ for the different species 22, 24. As depicted, each species 22, 24 has a different peak corresponding to the most instances of residence times, the peaks corresponding respectively to residence times $R_\diamond, R_\circ$. As residence times are different for different species, this information is useful in identifying the species 22, 24.

During operation of the sensing system 10, the adsorption and desorption properties of the nano-transducer 12 may be modified. The controlled surface S of the nano-transducer may be subjected to conditions so that preferential adsorption and/or desorption results. It is believed that adsorption and desorption rates may be temperature dependent, illumination dependent, and/or electrically dependent. As such, time-dependent modification of the nano-transducer 12 temperature, optical illumination conditions, or electrical state conditions may further assist in identifying the target species 22, 24. Without being bound to any theory, it is believed that time-dependent modification alters the response of the nano-transducer 12 to various target species 22, 24, thereby increasing the nano-transducer 12 specificity. It is to be understood that the conditions may be changed, i.e., dynamically controlled, if, and as often as desirable throughout the sensing process.

In an embodiment, the nano-transducer 12 is temperature controlled. The adsorption or desorption of a species 22, 24 on, or from the nano-transducer 12 surface S may be affected by a change in temperature. It is to be understood that the surface S temperature may be altered by heating or cooling the nano-transducer 12, or by heating or cooling an environment to which the nano-transducer 12 is exposed. As a non-limiting example, a temperature ramp may be applied to the nano-transducer 12 after adsorption of a species 22, 24 has occurred for a short time at room temperature. Generally, the species 22, 24 will desorb at a rate that is characteristic of the species 22, 24 and the controlled surface S or receptor 20. This type of temperature control may be referred to as temperature programmed desorption. It is believed that temperature programmed desorption may be particularly effective if the nano-transducer 12 is a resistive element that readily changes temperature upon application of current.

Another non-limiting example of the effect that temperature control has on the adsorption and desorption properties of a single nano-transducer 12 is depicted in FIGS. 5A, 5B and 5C. In this example embodiment, the temperature of the nano-transducer controlled surface S is increased over time. The graph labeled T1 (shown in FIG. 5A) illustrates the distribution of residence times $R_\diamond$, $R_\circ$ for two species 22 ($\diamond$), 24 ($\circ$) when the single nano-transducer 12 is exposed to a first temperature for a predetermined time period. The graph labeled T2 (shown in FIG. 5B) illustrates the distribution of the residence times $R_\diamond$, $R_\circ$ for the same two species shown in graph T1 when the single nano-transducer 12 is exposed to a second temperature (greater than the first temperature) for a second predetermined time period. Finally, the graph labeled T3 (shown in FIG. 5C) illustrates the distribution of residence times $R_\diamond$, $R_\circ$, for the species 22, 24 when the single nano-transducer 12 is exposed to a third temperature (greater than the first two temperatures) for a third predetermined time period. As shown in the graphs, the distribution of residence times $R(R_\diamond$, $R_\circ$ for at least one of the species 22, 24 changes as the temperature changes. Since the residence times $R_\diamond$, $R_\circ$, are extracted from adsorption and desorption events, it is to be understood that the temperature changes may assist in controlling adsorption and/or desorption.

As described further hereinbelow with reference to an array of nano-transducers 12, the graphs shown in FIGS. 5A, 5B and 5C may also be illustrative of the effect of different nano-transducers 12 in an array at temperatures T1, T2 and T3, respectively.

In an embodiment, the nano-transducer 12 is illumination controlled. Illumination control generally means that the controlled surface S is sensitive to a particular wavelength or range of wavelengths (e.g., ranging from IR to deep UV wavelengths). The adsorption or desorption of a species 22, 24 on, or from the nano-transducer 12 controlled surface S may be affected by a change in an optical illumination condition of the nano-transducer 12. Exposing the nano-transducer surface S to a particular wavelength or range of wavelengths may determine which species 22, 24 is capable of adsorbing thereon and/or may change the residence time R for one or more species 22, 24 (i.e., may alter desorption). In an embodiment, the controlled surface S may be inert to adsorption of a species 22, 24, until the surface S is exposed to a particular wavelength or range of wavelengths of light. As such, a particular wavelength or range of wavelengths may be used to activate the controlled surface S. Conversely, the controlled surface S may be configured to adsorb a species 22, 24, until the surface S is exposed to a particular wavelength or range of wavelengths of light. As such, a particular wavelength or range of wavelengths may be used to inactivate the controlled surface S. In another embodiment, a change in illumination may be applied to the nano-transducer 12 after adsorption of a species 22, 24 has occurred at some predetermined illumination condition. Generally, the species 22, 24 will desorb at a rate that is characteristic of the species 22, 24, the controlled surface S or receptor 20, and the illumination condition. In another embodiment, a particular species 22, 24 may be chemically modified by the light, such that the chemically modified species preferentially adsorbs to the nano-transducer 12.

In still another embodiment, the nano-transducer 12 is electrically controlled. Electrical control generally means that the controlled surface S is sensitive to a particular electrical state. As used herein, the term "electrical state" is meant to include a local electric field, an electrical event sequence, a bias, or the like, or combinations thereof. The adsorption or desorption of a species 22, 24 on, or from the nano-transducer 12 controlled surface S may be affected by a change in the electrical state to which the nano-transducer 12 is exposed. Introducing or changing the electrical state may determine which species 22, 24 is capable of adsorbing on the surface S (or receptor 20 thereon) and/or may change the residence time R for one or more species 22, 24 (i.e., may alter desorption). As a non-limitative example, the controlled surface S may be activated by the introduction of the electrical state. As such, the surface S may be inert to adsorption of a species 22, 24, until it is exposed to a particular electrical state. As another non-limiting example, a change in the electrical state may be applied to the nano-transducer 12 after adsorption of a species 22, 24 has occurred, for example, in the absence of an electrical state or at some predetermined electrical state. In response to the electrical state change, the species 22, 24 will desorb at a rate that is characteristic of the species 22, 24, the controlled surface S or receptor 20, and the electrical state. The electrical state may be generated from a pair of electrodes that is external to the sensing system 10. In an embodiment in which the sensing system 10 is an electrical sensing system, electrode 14, 16 may be used to generate or change the electrical state.

Figures 6, 7B:
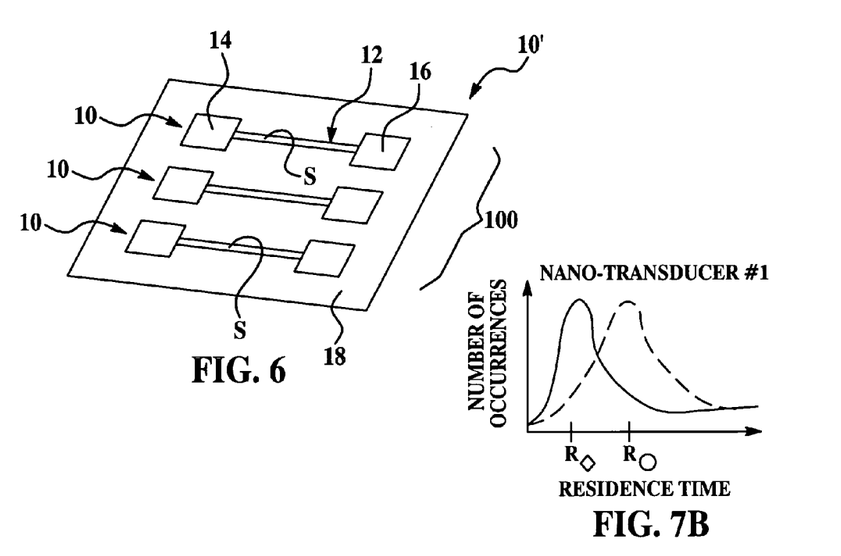
FIG. 6 is a schematic top view of an embodiment of the sensing system including an array of nano-transducers.
FIGS. 7B, 7C and 7D depict graphs illustrating example distributions of residence times of two different species on the different nano-transducers shown in FIG. 7A.

Referring now to FIG. 6, another embodiment of a sensing system 10' is shown. This embodiment includes an array 100 of individual sensing systems 10. More specifically, the array 100 includes a number of nano-transducers 12, each of which has a controlled surface S (e.g., receptors 20 established thereon, a predetermined atomic composition, a predetermined nanostructure, or combinations thereof). While each of the individual sensing systems 10 is shown as an electrical sensing system having electrodes 14, 16, it is to be understood that the systems 10 in the array 100 may also be optical or mechanical sensing systems, and thus may not include either or both electrodes 14, 16. Each of the nano-transducers 12 in the array 100 is configured to transduce (electrically, optically or mechanically) individual adsorption and desorption events into measurable signals, as previously described hereinabove in reference to the sensing system 10.

Figure 7A:
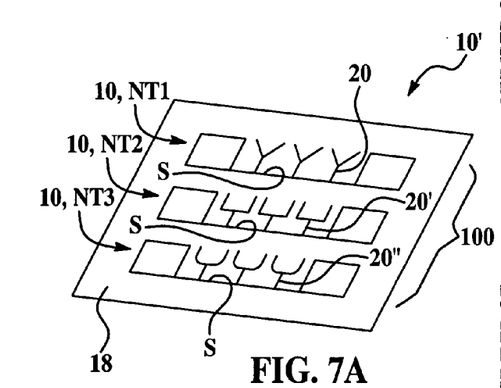
FIG. 7A is a schematic view of an embodiment of a sensing system including an array of nano-transducers, each having a different controlled surface.
Figure 7C:
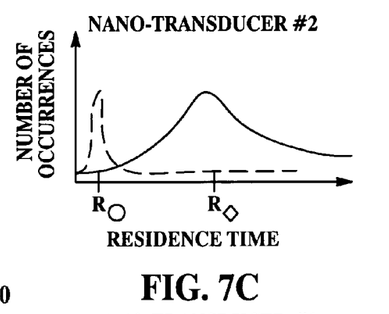
Figure 7D:
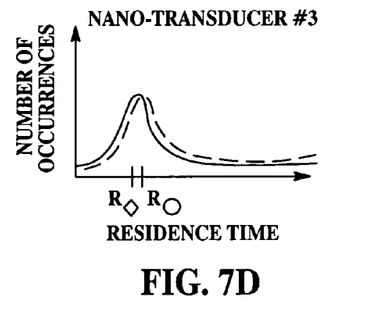

In this embodiment of the sensing system 10', one or more of the controlled surfaces S may be differentiated from at least one other of the controlled surfaces S. For example, at least one of the controlled surfaces S may be functionalized to preferentially adsorb and desorb a different species 22, 24 than at least one other of the controlled surfaces S in the array 100. An embodiment of a sensing system 10' having differentiated nano-transducers 12 is shown in FIG. 7A. As depicted, each of the nano-transducers 12 has a controlled surface S defined by a different type of receptor 20, 20', 20". FIGS. 7B, 7C and 7D illustrate the type of statistical distribution of resident times R that may be extracted from the plurality of individual adsorption and desorption events and residence times R of species 22 ($\diamond$), 24 ($\circ$) that are detected. In this non-limiting example, each of the nano-transducers 12 (NT1 (FIG. 7B), NT2 (FIG. 7C), NT3 (FIG. 7D)) adsorbs and desorbs the different species 22, 24. The different adsorption and desorption behaviors exhibited by the species 22, 24 occurs, in part, because of the different functionalities of the controlled surfaces S. Analysis of the different distribution of residence times assists in substantially identifying the target species 22, 24.

It is to be understood that at least one of the nano-transducers 12 in the array 100 may also exhibit a characteristic that is different from at least one other of the nano-transducers 12 in the array 100. Non-limiting examples of such characteristics include geometry (e.g., thickness, shape, etc.), size, atomic composition (e.g., Si, Ge, SiGe, GaAs, some —$CH_3$ species, etc.), doping distribution, temperature, illumination, electrical state, and/or combinations thereof. The different characteristics of one or more of the nano-transducers 12 in the array 100 allows the sensing system 10' to detect and identify a variety of different species 22, 24 at different times and under different conditions.

In an embodiment, each of the nano-transducers 12 in the array 100 may have different controlled surfaces S and/or exhibit different characteristics from any other nano-transducer 12 in the array 100. In an alternate embodiment, some of the nano-transducers 12 in the array 100 may have different controlled surfaces S and/or exhibit different characteristics from some other nano-transducers 12 in the array 100.

As the nano-transducers 12 in the array 100 may be configured to preferentially and/or differentially adsorb and desorb under different conditions, a change in one or more of the conditions may result in the alteration of the adsorption and desorption properties of one or more of the nano-transducers 12, while others in the array 100 remain unaffected. Furthermore, the conditions may be altered again at a later time so that other adsorption and/or desorption properties of other nano-transducers 12 in the array 100 are altered. Time-dependent modification of the adsorption and/or desorption of at least some of the nano-transducers 12 in the array 100 may be achieved via temperature control, illumination control, and/or electrical state control, as previously described.

In an embodiment, one or more of the nano-transducer 12 in the array 100 is temperature controlled. The adsorption or desorption of a species 22, 24 on, or from the nano-transducer 12 surfaces S may be affected by a change in temperature. As previously described, the graphs shown in FIGS. 5A, 5B and 5C may be examples of the effect that temperature control has on the adsorption and desorption properties of each nano-transducer 12 in an array 100. In this example embodiment, the temperature across the array 100 is a gradient, where a first nano-transducer 12 in the array 100 is exposed to a first temperature, a second nano-transducer 12 is exposed to a different second temperature, and a third nano-transducer 12 is exposed to a different third temperature. In this embodiment, the graphs labeled T1 (shown in FIG. 5A), T2 (shown in FIG. 5B) and T3 (shown in FIG. 5C) illustrate the type of distribution of residence times $R_\diamond$, $R_\circ$ that may be extracted for two species 22 ($\diamond$), 24 ($\circ$) that adsorb and desorb on, and from the first, second, and third nano-transducers 12, respectively. As shown in the graphs, the distribution of residence times $R(R_\diamond, R_\circ)$ for the species 22, 24 may change for each of the nano-transducers 12 that is independently sensitive to different temperature conditions.

In another embodiment, one or more of the nano-transducers 12 in the array 100 is illumination controlled. The adsorption or desorption of a species 22, 24 on, or from the nano-transducer 12 surfaces S may be affected by exposure to a particular wavelength or range of wavelengths. Some of the surfaces S may be activated by a particular wavelength or range of wavelengths, while others may be deactivated or unaffected by such a wavelength or range of wavelengths. As such, the adsorption and/or desorption of at least some of the nano-transducers 26 in the array 100 may be tuned via illumination.

In still another embodiment, one or more of the nano-transducers 12 in the array 100 is electrically controlled. Some of the controlled surfaces S of the nano-transducers 12 in the array 100 may be sensitive to a particular electrical state. As such, exposure to a local electrical state may alter the adsorption or desorption of a species 22, 24 on, or from one or more of nano-transducers 12.

In any of the embodiments disclosed herein, a database of general species 22, 24 information (e.g., kinetic capture and release rate characteristics, interaction with controlled surfaces, etc.) may be constructed in order to perform statistical data matching. Data matching generally includes comparing the responses of known species to the responses of unknown species which are being identified or quantified. The telegraph signals and histograms formulated using adsorption events, desorption events and residence times may be compared with known information to identify the target species 22, 24 using any of the many well-known statistical methods.

Embodiments of the sensing system 10, 10' disclosed herein may also include a micro- or nano-sample pre-separation unit. Such units are used to separate mixtures to reduce their complexity, such that nano-transducers 12 are exposed to a reduced number of species at any given time. Examples of pre-separation mechanisms include, but are not limited to, solid phase extraction, liquid-liquid extraction, gel permeation, thermal desorption, mass separation, any of numerous forms of chromatography, or the like, or combinations thereof. It is believed that the pre-separation unit is useful for minimizing the interference of multiple species from the environment, and increasing detection sensitivity of the sensing system 10, 10'.

Figure 8A:
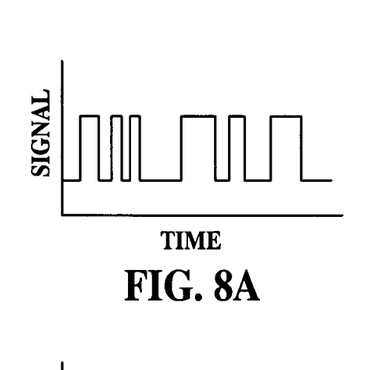
FIGS. 8A and 8B depict example signal versus time graphs for embodiments of the nano-transducer exposed to dilute and concentrated samples, respectively.
Figure 8B:
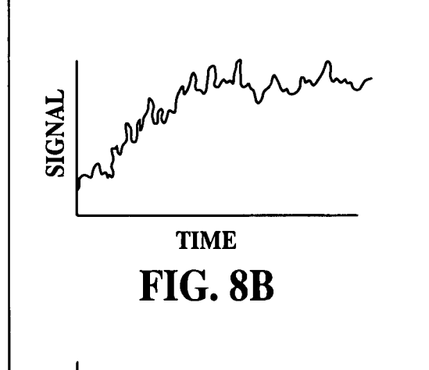

FIGS. 8A and 8B illustrate the differences between a single sensing system 10 (as disclosed herein) when exposed to a dilute sample and a concentrated sample. As depicted, the nano-transducers 12 of the sensing system 10 may become saturated (FIG. 8B) when exposed to a concentrated sample, and this may result in the inability to extract residence times R for one or more of the species 22, 24 in the sample (for further details, see FIGS. 9A through 9C). In sharp contrast, however, when the nano-transducers 12 are exposed to a dilute sample, individual adsorption and desorption events are detectable, and residence times R are extractable and useful for species 22, 24 identification and quantification.

Figure 8C:
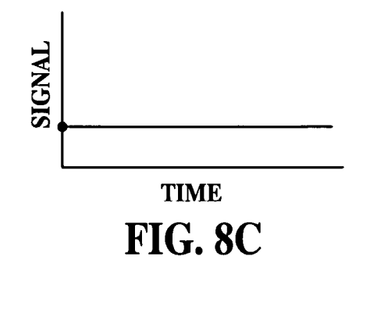
FIGS. 8C and 8D depict example signal versus time graphs for a transducer (that is unable to recognize individual events) exposed to dilute and concentrated samples, respectively.
Figure 8D:
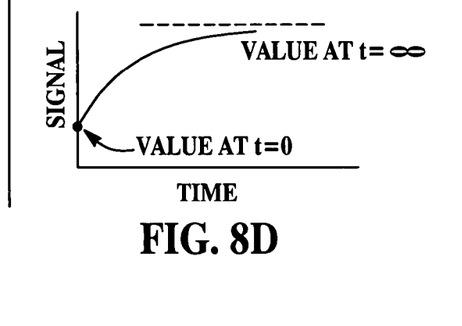

FIGS. 8C and 8D illustrate the signals that are obtained when other transducers (i.e., those that are not sensitive to individual adsorption and/or desorption events) are exposed to dilute and concentrated samples. As depicted in FIG. 8C, when exposed to a dilute sample, the transducer is generally unable to detect any species 22, 24. As depicted in FIG. 8D, when exposed to a concentrated sample, the transducer is capable of detecting several events, but is unable to recognize individual adsorption and desorption events.

Figure 9A:
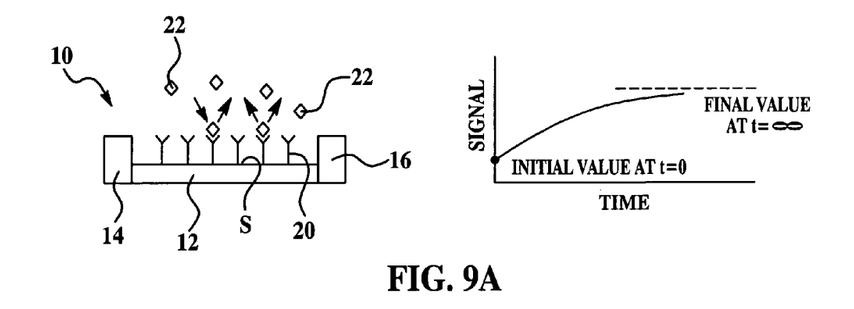
FIG. 9A depicts a schematic side view of an embodiment of a sensing system having receptors established thereon when exposed to a concentrated sample including a first species, and a corresponding signal versus time graph.
Figure 9B:
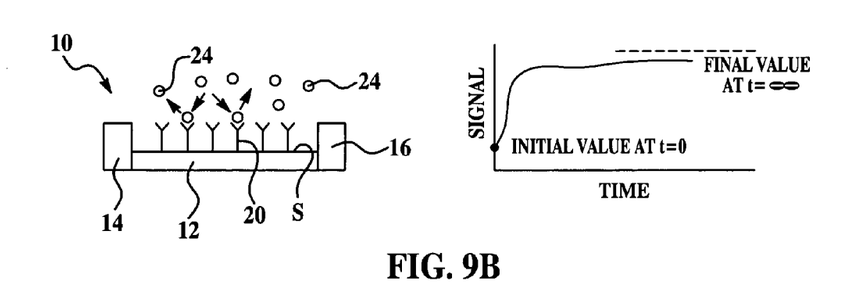
FIG. 9B depicts a schematic side view of an embodiment of a sensing system having receptors established thereon when exposed to a concentrated sample including a second species, and a corresponding signal versus time graph.
Figure 9C:
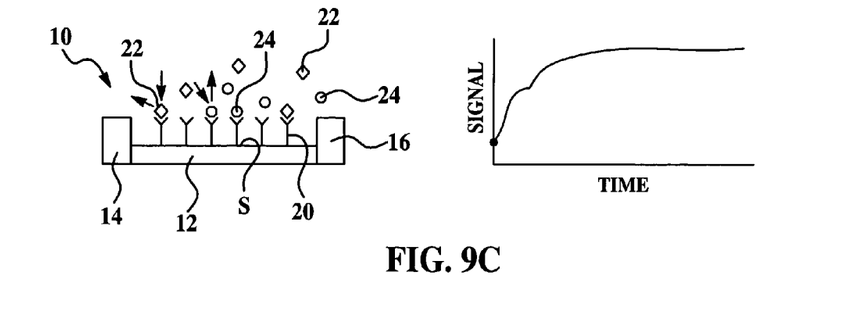
FIG. 9C depicts a schematic side view of an embodiment of a sensing system having receptors established thereon when exposed to a concentrated sample including first and second species, and a corresponding example signal versus time graph.

Referring now to FIGS. 9A through 9C, embodiments of the sensing system 10 exposed to concentrated samples and corresponding signal versus time graphs are depicted. In FIG. 9A specifically, the sensing system 10 includes a plurality of receptors 20 forming the controlled surface S. The system 10 is exposed to a concentrated sample containing species 22. As shown in the corresponding signal versus time graph, the signals detected generally result in a smooth curve indicative of several events (as opposed to a telegraph signal indicative of individual events). It is believed that while statistical distributions may not be determined, the shape of the curve may yet be useful in identifying the species 22.

FIG. 9B depicts the sensing system 10 of FIG. 9A exposed to a concentrated sample containing species 24. As shown in the corresponding signal versus time graph, the signals detected generally result in a smooth curve indicative of several events (as opposed to a telegraph signal indicative of individual events). Again, it is believed that while statistical distributions may not be determined, the shape of the curve may be useful in identifying the species 24.

FIG. 9C depicts the sensing system 10 of FIGS. 9A and 9B exposed to a concentrated sample containing both species 22, 24. As shown in the corresponding signal versus time graph, the signals from both the species 22, 24 are detected, and the single smooth curve is indicative of several events of both the species 22, 24 (as opposed to a telegraph signal indicative of individual events of each species 22, 24). It is believed that while statistical distributions may not be determined, the shape of the curve may, in some instances, be of some use in identifying both of the species 22, 24 (though a curve of this type may not be as useful as the type of curves shown in FIGS. 9A and 9B).

The graphs depicted in FIGS. 9A through 9C may be particularly useful to determine when sample dilution may be desirable. As previously described, the smooth curves are indicative of the inability to detect individual events. If detection of individual events is desired, the smooth curve indicates that sample dilution may be desirable. The concentrated samples may be diluted with a substantially pure make up gas (e.g., pure air, nitrogen or helium) or liquid in an automated, or other suitable fashion. Such dilution and measurements may be taken until unique individual events become observable.

To further illustrate embodiment(s) of the present disclosure, an example is given herein. It is to be understood that this example is provided for illustrative purposes and is not to be construed as limiting the scope of the disclosed embodiment(s).

EXAMPLE

Illustrated is a simplified example of identifying an organic molecule containing a combination of two or more of the four functional groups or characteristics listed in column 1 of Table 1.

TABLE 1

Receptors and Corresponding Targets

| Target Functional Group | Target Functional Group Examples | Corresponding Receptor Functional Group | Receptor Functional Group Examples |
|---|---|---|---|
| e-acceptors | -φ-BH$_2$ | e-donors | —Si—OH |
| e-donors | —OH, —NH$_2$ | e-acceptors | —Si—BCl$_2$ |
| Aromatics | Benzene | aromatics | —Si-φ |
| Polar | —NO$_2$, —CN | polar groups | —Si—NO$_2$ |

Notes: φ = phenyl

Four corresponding classes of receptors 20 (see column 4 of Table 1) are selected to functionalize the surface of a silicon nanowire. One or more of the receptors 20 has an affinity to a particular target functional group of the unknown, which is suspected to be tri-nitro-toluene (TNT) (Formula (I) below). The highly polar NO$_2$ groups are likely to adsorb on and desorb from the polar receptor, and the aromatic ring is likely to adsorb on and desorb from the Si-φ receptor. Such adsorption and desorption events are transducable to measurable signals. The signals transduced from the adsorption and desorption of the TNT functional groups are believed to provide a signature for tri-nitro-toluene. This signature is believed to be different from that of another molecule such as cyclotrimethylenetrinitramine (Formula (II) below), which does not have an aromatic ring but has nitrogen atoms that are weak e-donors.

While several embodiments have been described in detail, it will be apparent to those skilled in the art that the disclosed embodiments may be modified. Therefore, the foregoing description is to be considered exemplary rather than limiting.

What is claimed is:

1. A sensing method, comprising:
   exposing a nano-transducer having a controlled surface to a sample including at least one species;
   transducing adsorption of the at least one species on the nano-transducer, to a measurable signal as a function of time;
   transducing desorption of the at least one species from the nano-transducer to a measurable signal as a function of time; and
   extracting from the measurable signals a residence time of the at least one species adsorbed on the nano-transducer;
   wherein the adsorption and desorption each define an individual measurable event.

2. The sensing method as defined in claim 1 wherein an individual measurable event includes a small integer number of adsorptions, desorptions or combinations thereof of the at least one species.

3. The sensing method as defined in claim 1, further comprising extracting statistical data from a plurality of the individual adsorption and desorption events and the residence times in a manner sufficient to substantially identify the at least one species.

4. The sensing method as defined in claim 1 wherein prior to exposing, the method further comprises functionalizing the nano-transducer with at least one receptor, the at least one receptor configured to preferentially adsorb and desorb one or more species.

5. The sensing method as defined in claim 1 wherein transducing is accomplished electrically, mechanically, optically, or via combinations thereof.

6. The sensing method as defined in claim 1, further comprising time-dependent modification of adsorption properties, desorption properties, or combinations thereof of the nano-transducer.

7. The sensing method as defined in claim 6 wherein time-dependent modification is accomplished by at least one of changing a temperature of the nano-transducer surface, changing an optical illumination condition of the nano-transducer, changing a local electrical state to which the nano-transducer is exposed, or combinations thereof.

8. The sensing method as defined in claim 1 wherein the controlled surface of the nano-transducer has: at least one receptor established thereon, a controlled atomic composition, a controlled nanostructure, or combinations thereof.

9. A sensing method, comprising:
exposing an array of nano-transducers to a sample including at least one species, each of the nano-transducers in the array having a controlled surface;
transducing adsorption of the at least one species on at least one of the nano-transducers in the array, to a measurable signal as a function of time;
transducing desorption of the at least one species from the at least one of the nano-transducers in the array, to a measurable signal as a function of time; and
extracting from the measurable signals a residence time of the at least one species adsorbed on the at least one of the nano-transducers in the array;
wherein the adsorption and desorption each define an individual measurable event.

10. The sensing method as defined in claim 9 wherein an individual measurable event includes a small integer number of adsorptions, desorptions or combinations thereof of the at least one species.

11. The sensing method as defined in claim 9, further comprising extracting statistical data from a plurality of the individual adsorption and desorption events and the residence times in a manner sufficient to substantially identify the at least one species.

12. The sensing method as defined in claim 9 wherein prior to exposing, the method further comprises functionalizing at least two of the nano-transducers with at least one receptor, wherein the at least one receptor on one of the at least two nano-transducers is configured to preferentially adsorb and desorb a different species than the at least one receptor on an other of the at least two nano-transducers.

13. The sensing method as defined in claim 9 wherein transducing is accomplished electrically, mechanically, optically, or via combinations thereof.

14. The sensing method as defined in claim 9 wherein at least one of the nano-transducers exhibits a characteristic that is different from at least one other of the nano-transducers, and wherein the characteristic is selected from geometry, size, atomic composition, doping distribution, temperature, illumination, local electrical state, and combinations thereof.

15. The sensing method as defined in claim 9, further comprising time-dependent modification of adsorption properties, desorption properties, or combinations thereof of at least one of the nano-transducers in the array.

16. The sensing method as defined in claim 15 wherein time-dependent modification is accomplished by at least one of changing temperature conditions to which the array is exposed, changing an optical illumination condition of the array, changing a distribution of an electrical state across the array, or combinations thereof.

17. The sensing method as defined in claim 9 wherein the controlled surface of each of the nano-transducers has: at least one receptor established thereon, a controlled atomic composition, a controlled nanostructure, or combinations thereof.

18. A nanosensing system, comprising at least one nano-transducer having a controlled surface, the nano-transducer being configured to transduce adsorption and desorption of at least one species to a measurable signal as a function of time, wherein the adsorption and desorption each define an individual measurable event and wherein a residence time of the at least one species adsorbed on the nano-transducer is extractable from the measurable signals.

19. The nanosensing system as defined in claim 18 wherein the at least one nano-transducer exhibits a characteristic selected from a predetermined geometry, a predetermined size, a predetermined atomic composition, a predetermined doping distribution, a predetermined temperature, a predetermined illumination, a predetermined local electrical state, and combinations thereof.

20. The nanosensing system as defined in claim 18 wherein the controlled surface is a time-dependent modified surface, the time-dependent modification configured to chemically or physically modulate the controlled surface to preferentially adsorb or desorb the at least one species.

21. The nanosensing system as defined in claim 20 wherein the time-dependent modification is accomplished by at least one of changing temperature conditions to which the at least one nano-transducer is exposed, changing an optical illumination condition of the at least one nano-transducer, changing a distribution of an electrical state across the at least one nano-transducer, or combinations thereof.

22. The nanosensing system as defined in claim 18 wherein the controlled surface of the at least one nano-transducer has: at least one receptor established thereon; a controlled atomic composition; a controlled nanostructure; or combinations thereof.

23. The nanosensing system as defined in claim 18 wherein the at least one nano-transducer is selected from a metal nanowire, a semiconductor nanowire, and combinations thereof, and wherein at least two dimensions of the nano-transducer are nanometer scale.

24. The nanosensing system as defined in claim 18 wherein the at least one nano-transducer is at least one of an array of nano-transducers.

25. The nanosensing system as defined in claim 18, further comprising a micro- or nano-sample pre-separation unit to isolate and separate a crude sample into at least one substantially pure sample fragment.

26. The nanosensing system as defined in claim 18 wherein an individual measurable event includes a small integer number of adsorptions, desorptions or combinations thereof of the at least one species.

27. The nanosensing system as defined in claim 26 wherein statistical data is extractable from a plurality of the individual adsorption and desorption events and the residence times.

* * * * *